US012765817B2

(12) United States Patent
Park et al.

(10) Patent No.: US 12,765,817 B2
(45) Date of Patent: Oct. 20, 2026

(54) SAMPLE PAD FOR MEDICAL DIAGNOSIS KIT, AND PRODUCTION METHOD THEREFOR

(71) Applicant: ENVIONEER CO., LTD, Jecheon-si (KR)

(72) Inventors: Seong Eun Park, Suwon-si (KR); Byeong Joon Lee, Daegu (KR); Ji Soo Won, Jecheon-si (KR); Woong Gi Jang, Wonju-si (KR)

(73) Assignee: ENVIONEER CO., LTD, Jecheon-si (KR)

( * ) Notice: Subject to any disclaimer, the term of this patent is extended or adjusted under 35 U.S.C. 154(b) by 714 days.

(21) Appl. No.: 18/012,568

(22) PCT Filed: Feb. 17, 2021

(86) PCT No.: PCT/KR2021/002044

§ 371 (c)(1),
(2) Date: Dec. 22, 2022

(87) PCT Pub. No.: WO2022/014810

PCT Pub. Date: Jan. 20, 2022

(65) Prior Publication Data

US 2023/0255528 A1 Aug. 17, 2023

(30) Foreign Application Priority Data

Jul. 15, 2020 (KR) ........................ 10-2020-0087169

(51) Int. Cl.
*A61B 5/15* (2006.01)
*D21H 21/20* (2006.01)

(52) U.S. Cl.
CPC ....... *A61B 5/150206* (2013.01); *D21H 21/20* (2013.01)

(58) Field of Classification Search
CPC .......................... A61B 5/150206; D21H 21/20
See application file for complete search history.

(56) References Cited

U.S. PATENT DOCUMENTS

| | | | | |
|---|---|---|---|---|
| 5,821,179 | A | 10/1998 | Masaki et al. | |
| 2003/0003830 | A1 | 1/2003 | Quederni et al. | |
| 2003/0194552 | A1 | 10/2003 | Pittman et al. | |
| 2004/0154763 | A1 | 8/2004 | Polat et al. | |
| 2004/0157524 | A1 | 8/2004 | Polat et al. | |
| 2007/0232180 | A1 | 10/2007 | Polat et al. | |
| 2009/0199349 | A1 * | 8/2009 | Weinstein | D06M 15/263 8/120 |

(Continued)

FOREIGN PATENT DOCUMENTS

| | | | |
|---|---|---|---|
| CN | 1450211 | A | 10/2003 |
| CN | 101404969 | A | 4/2009 |

(Continued)

*Primary Examiner* — Abbas Rashid
*Assistant Examiner* — Stephen M Russell
(74) *Attorney, Agent, or Firm* — Birch, Stewart, Kolasch & Birch, LLP

(57) ABSTRACT

The present invention relates to a sample pad for a medical diagnosis kit, and a production method therefor, and more specifically relates to a sample pad for a medical diagnosis kit, the sample pad being characterized by comprising softwood pulp, PET fibres, binder fibres, and a wet-strength enhancer, and a production method therefor.

5 Claims, 1 Drawing Sheet

(56) References Cited

U.S. PATENT DOCUMENTS

| | | | | |
|---|---|---|---|---|
| 2011/0168342 | A1 | 7/2011 | Mohammadi | |
| 2011/0220310 | A1 | 9/2011 | Polat et al. | |
| 2012/0156466 | A1* | 6/2012 | Bell | F41H 5/0471 428/297.4 |
| 2015/0233060 | A1 | 8/2015 | Polat et al. | |
| 2017/0079856 | A1 | 3/2017 | Kimura et al. | |
| 2018/0325755 | A1* | 11/2018 | Qin | D21H 21/20 |
| 2020/0063358 | A1* | 2/2020 | Everett | D21H 17/17 |
| 2020/0283958 | A1 | 9/2020 | Mustonen et al. | |

FOREIGN PATENT DOCUMENTS

| | | | |
|---|---|---|---|
| CN | 107656050 | A | 2/2018 |
| EP | 0 719 531 | A1 | 7/1996 |
| KR | 10-2007-0018490 | A | 2/2007 |
| KR | 10-0839215 | B1 | 7/2008 |
| KR | 10-1207933 | B1 | 12/2012 |
| KR | 10-1396321 | B1 | 5/2014 |
| KR | 10-2017-0025813 | A | 3/2017 |
| KR | 10-1754907 | B1 | 7/2017 |
| KR | 10-1895789 | B1 | 9/2018 |
| KR | 10-2019-0071841 | A | 6/2019 |
| KR | 10-2003648 | B1 | 7/2019 |
| KR | 10-2181097 | B1 | 11/2020 |
| WO | WO 2017/079310 | A1 | 5/2017 |
| WO | WO 2017/203101 | A1 | 11/2017 |

* cited by examiner

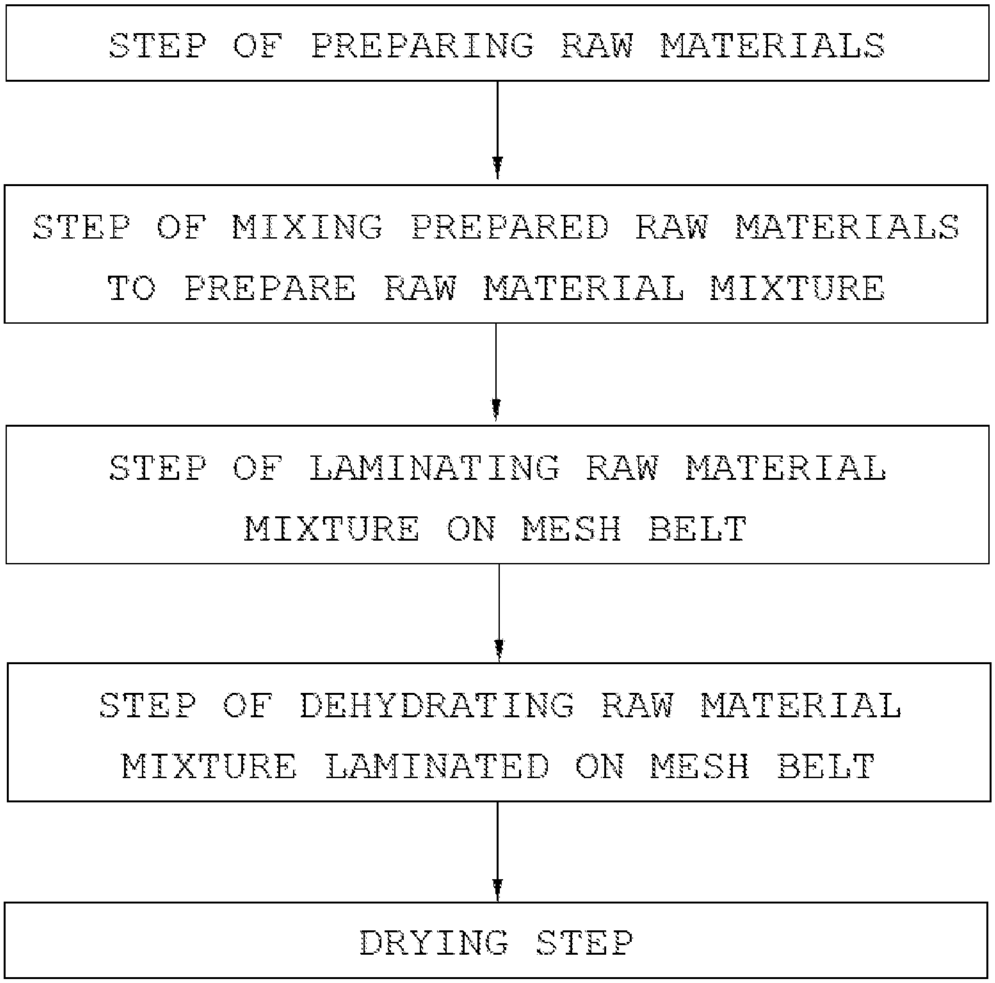
STEP OF PREPARING RAW MATERIALS
STEP OF MIXING PREPARED RAW MATERIALS TO PREPARE RAW MATERIAL MIXTURE
STEP OF LAMINATING RAW MATERIAL MIXTURE ON MESH BELT
STEP OF DEHYDRATING RAW MATERIAL MIXTURE LAMINATED ON MESH BELT
DRYING STEP

SAMPLE PAD FOR MEDICAL DIAGNOSIS KIT, AND PRODUCTION METHOD THEREFOR

TECHNICAL FIELD

This application is the National Phase of PCT International Application No. PCT/KR2021/002044, filed on Feb. 17, 2021, which claims priority under 35 U.S.C. 119(a) to Patent Application No. 10-2020-0087169, filed in the Republic of Korea on Jul. 15, 2020, all of these applications being hereby expressly incorporated by reference into the present application.

The present invention relates to a sample pad for medical diagnosis kits and a method of manufacturing the same, and more particularly to a sample pad for medical diagnosis kits, wherein the sample pad includes a coniferous pulp, a PET fiber, a binder fiber, and a wet strengthening agent, whereby the surface smoothness, water absorption, and wicking rate of the sample pad are high, and a method of manufacturing the same.

BACKGROUND ART

Various diseases exist on the earth, and existence of viruses was known only in the 20th century. In recent years, new variant viruses have been generated.

In particular, with spread of contagious diseases, such as germs and viruses, demand for diagnosis kits capable of checking whether infection has occurred has increased, and there is a need for technology related to diagnosis as the result of generation of variants or new viruses.

A medical diagnosis kit, which is a kit that enables pregnancy diagnosis and testing for various diseases, such as cancers, using antigen-antibody reaction, has been widely used since the medical diagnosis kit has an advantage in that the medical diagnosis kit enables a sample, such as blood, spit, or urine to react with a specific drug in order to simply check whether infected by a specific disease.

The medical diagnosis kit generally includes a sample pad configured to allow a sample to be tested (or an analysis solution) to drip so as to be absorbed thereinto, a conjugate pad treated with a colored particle (colloidal gold, colored polystyrene nanoparticle, etc.) configured to react with the sample absorbed into the sample pad, a membrane pad configured to show a colored detection result (test line/control line) as the result of movement of the colored particle in the conjugate pad (the membrane pad is a pad having a test line and a control line and is generally made of nitrocellulose), and an absorption pad configured to finally absorb the sample that has passed through the membrane pad.

Thereamong, the sample pad, which is configured to allow the sample to be tested (or the analysis solution) to drip so as to be absorbed thereinto, transmits the sample to the conjugate pad in a state of being mixed with a buffer solution at an appropriate speed (rate) in an appropriate direction such that the sample reacts with the test line in the membrane pad (the pad having the test line and the control line, which is generally made of nitrocellulose).

The sample pad, which is generally made of pulp-based non-woven fabric, is required to perform accurate water absorption at a high wicking rate so as to have a uniform amount of water absorption, and the thickness and surface smoothness of the sample pad must be maintained within an error range corresponding to the size of the medical diagnosis kit.

If the sample pad is defective, the test line/control line does not react or reaction is nonuniform, whereby a test failure possibility is increased.

PRIOR ART DOCUMENTS (Patent Document 1) Korean Registered Patent Publication No. 1396321

(Patent Document 2) Korean Registered Patent Publication No. 1207933

DISCLOSURE

Technical Problem

The present invention has been made in view of the above problems, and it is an object of the present invention to provide a sample pad for medical diagnosis kits having uniform water absorption and high wicking rate and a method of manufacturing the same.

It is another object of the present invention to provide a sample pad for medical diagnosis kits having excellent surface smoothness and a significantly low defect rate and a method of manufacturing the same.

Technical Solution

In order to accomplish the above objects, a sample pad according to the present invention includes a coniferous pulp, a PET fiber, a binder fiber, and a wet strengthening agent.

Also, in the sample pad according to the present invention, 60 to 75 parts by weight of the coniferous pulp, 10 to 20 parts by weight of the PET fiber, 10 to 20 parts by weight of the binder fiber, and 1 to 5 parts by weight of the wet strengthening agent may be included.

Also, in the sample pad according to the present invention, the coniferous pulp may have a length of 2.0 to 3.0 mm, the PET fiber may have a diameter of 1 to 3 de and a length of 3 to 12 mm, the binder fiber may be low melting point polyethylene terephthalate (PET) having an average melting point of 100° C. to 150° C., and the wet strengthening agent may be an epoxy-based resin.

Also, in the sample pad according to the present invention, the sample pad may be configured such that a wicking rate of 24 to 28 sec/4 cm and a water absorption of 60 to 70 $mg/cm^2$ are satisfied.

Also, in the sample pad according to the present invention, the sample pad may be used for medical diagnosis kits.

In addition, a method of manufacturing a sample pad according to the present invention includes (a) preparing raw materials, (b) mixing the prepared raw materials to prepare a raw material mixture, (c) laminating the raw material mixture on a mesh belt, and (d) dehydrating the raw material mixture laminated on the mesh belt.

Also, in the method of manufacturing the sample pad according to the present invention, the raw materials in step (a) may be an aqueous wet strengthening agent solution, a coniferous pulp, a PET fiber, and a binder fiber.

Also, in the method of manufacturing the sample pad according to the present invention, in step (b), 60 to 75 parts by weight of the coniferous pulp, 10 to 20 parts by weight of the PET fiber, and 10 to 20 parts by weight of the binder fiber may be mixed in 9,000 to 11,000 parts by weight of the aqueous wet strengthening agent solution, and the aqueous wet strengthening agent solution may include 9,000 to 11,000 parts by weight of water and 1 to 5 parts by weight of an epoxy resin.

Also, in the method of manufacturing the sample pad according to the present invention, in step (b), 60 to 75 parts by weight of the coniferous pulp, 10 to 20 parts by weight of the PET fiber, and 10 to 20 parts by weight of the binder fiber may be mixed in 9,500 to 10,500 parts by weight of the aqueous wet strengthening agent solution, and the aqueous wet strengthening agent solution may include 9,000 to 11,000 parts by weight of the water and 1 to 5 parts by weight of the epoxy resin.

Also, in the method of manufacturing the sample pad according to the present invention, step (d) may include a primary vacuum dehydration step of sequentially applying vacuum pressures of 0 to 5 cmHg, 10 to 20 cmHg, 30 to 40 cmHg, and 50 to 65 cmHg and a secondary vacuum dehydration step of applying a vacuum pressure of 18 to 22 cmHg.

Also, in the method of manufacturing the sample pad according to the present invention, (e) a drying step may be further performed after step (d), wherein in step (e), hot air drying at 110 to 130° C., hot air drying at 135 to 145° C., hot air drying at 100 to 110° C., and hot air drying at 135 to 145° C. may be sequentially performed.

Advantageous Effects

A sample pad for diagnosis kits according to the present invention and a method of manufacturing the same have a merit in that the sample pad includes a coniferous pulp and a binder fiber, whereby it is possible to provide a sample pad for diagnosis kits having high water absorption, wicking rate, and surface smoothness.

In addition, the sample pad for diagnosis kits according to the present invention and the method of manufacturing the same have an advantage in that a PET fiber and a wet strengthening agent are simultaneously added, whereby it is possible to inhibit paper fracture during a manufacturing process, and therefore it is possible to remarkably reduce a defect rate of the sample pad.

DESCRIPTION OF DRAWINGS

FIG. 1 is a flowchart illustrating a method of manufacturing a sample pad for diagnosis kits according to a preferred embodiment of the present invention.

BEST MODE

Hereinafter, the present invention will be described in more detail with reference to preferred embodiments of the present invention and the drawings. This means that the embodiments are described in detail to such an extent that a person having ordinary skill in the art to which the present invention pertains can easily implement the invention and do not limit the technical idea and category of the present invention.

All terms, including technical and scientific terms, have the same meanings as those commonly understood by one of ordinary skill in the art to which the present invention pertains, unless otherwise defined. Commonly used terms, such as those defined in typical dictionaries, should be interpreted as being consistent with the contextual meaning of the relevant art, and are not to be construed in an ideal or overly formal sense unless expressly defined to the contrary.

Hereinafter, a sample pad for medical diagnosis kits according to the present invention and a method of manufacturing the same will be described in detail.

First, the sample pad for medical diagnosis kits according to the present invention includes a coniferous pulp, a polyethylene terephthalate (PET) fiber, a binder fiber, and a wet strengthening agent.

In a basic mechanism of action of the sample pad, a capillary phenomenon due to porosity of the pad, which is a structural characteristic of the pad, and wettability of a raw material, which is a chemical characteristic of the raw material, occur in combination, whereby a liquid-state sample is horizontally and vertically moved in a solid-state sample pad.

When the sample pad is designed, therefore, a raw material having a physical structure and a chemical structure capable of satisfying both the capillary phenomenon and the wettability described above must be selected, and selection of a mixing ratio is very important.

The coniferous pulp that reveals strength characteristics of the sample pad such that the capillary phenomenon and the wettability can occur simultaneously preferably has a length of 2.0 to 3.0 mm, a coarseness 0.15 to 0.25 mg/m, and an initial freeness of 500 to 700 ml CSF, and more preferably has a length of 2.6 to 2.8 mm, a coarseness of 0.18 to 0.20 mg/m, and an initial freeness of 650 to 700 ml CSF.

The PET fiber is a material that is added such that the capillary phenomenon of the sample pad can be more securely realized. That is, as being mixed with the coniferous pulp, the PET fiber forms a flow path of the sample pad, and, as a result, the sample pad has a porous structure in all X, Y, and Z-axis directions. Of course, at least one of a polypropylene fiber, a carbon fiber, and a glass fiber may be further included, or any one thereof may be used instead of the PET fiber. However, a dispersant or a pH adjuster must also be added, and since the dispersant or the pH adjuster may remain in the sample pad, thereby affecting the result of detection, the PET fiber, which requires neither a dispersant nor pH adjustment, is most preferable.

Here, the PET fiber preferably has a diameter of 1 to 3 de and a length of 3 to 12 mm, and more preferably has a diameter of 1.5 to 2.5 de and a length of 3 to 6 mm.

The binder fiber binds the coniferous pulp and the PET fiber to each other to maintain the external shape of the sample pad.

In order to perform the above function, the binder fiber may be a low melting point fiber having an average melting point of 100° C. to 150° C., e.g. polyethylene terephthalate (PET) having a diameter of 1.5 to 2.5 de, a length of 5 to 7 mm, and a melting point of about 110° C.

Here, the low melting point polyethylene terephthalate preferably has a sheath-core structure such that appropriate pores can be formed at the time of binding, and the ratio of sheath to core is more preferably 3 to 7 (sheath):7 to 3 (core), and most preferably 5 (sheath) to 5 (core).

The wet strengthening agent is added in order to reduce paper fracture during a process and to maintain the shape of a sample and a buffer solution at the time of addition thereof.

In order to perform the above function, the wet strengthening agent is preferably made of a urea-formaldehyde resin, a melamine-formaldehyde resin, an epoxy resin, or polyethyleneimine (PEI). In particular, the epoxy-based resin is most preferable since the epoxy resin inhibits swelling of the PET fiber and the binder fiber, and therefore when the sample and an analysis solution are absorbed into the sample pad, the sample and the analysis solution are not deformed, whereby the sample and the analysis solution are smoothly movable.

Meanwhile, it is preferable for the coniferous pulp, the PET fiber, and the binder fiber to be mixed in a weight ratio of 60 to 75:5 to 25:10 to 20, and it is preferable for the wet strengthening agent to be added so as to account for 1 to 5 parts by weight.

If the content of the coniferous pulp is less than the above range, hygroscopicity is low, whereby the wicking rate of the sample is lowered when being applied to a diagnosis kit. If the content of the coniferous pulp is greater than the above range, on the other hand, hygroscopicity is excessively high. For these reasons, it is preferable for the content of the coniferous pulp to be within the above range.

If the content of the PET fiber is less than the above range, hygroscopicity is nonuniform. If the content of the PET fiber is greater than the above range, on the other hand, hygroscopicity is low, and wet strength is low. For these reasons, it is preferable for the content of the PET fiber to be within the above range.

Also, if the content of the binder fiber is less than the above range, the force of binding between fibers is low. If the content of the binder fiber is greater than the above range, on the other hand, the content of the coniferous pulp and the content of the PET fiber are relatively small, whereby hygroscopicity is low. For these reasons, it is preferable for the content of the binder fiber to be within the above range.

If the content of the wet strengthening agent is greater than the above range, hygroscopicity is low. If the content of the wet strengthening agent is less than the above range, wet strength is low. For these reasons, it is preferable for the content of the wet strengthening agent to be within the above range.

As a result, when the above mixing ratio is satisfied, the wicking rate, 24 to 28 sec/4 cm, and the water absorption, 60 to 70 mg/cm$^2$, of the sample pad required for medical diagnosis kits are simultaneously satisfied.

Next, a method of manufacturing a sample pad for diagnosis kits according to the present invention will be described. FIG. 1 is a flowchart illustrating a method of manufacturing a sample pad for diagnosis kits according to a preferred embodiment of the present invention.

As shown in FIG. 1, the method of manufacturing the sample pad for diagnosis kits according to the present invention includes (a) a step of preparing raw materials, (b) a step of mixing the prepared raw materials to prepare a raw material mixture, (c) a step of laminating the raw material mixture on a mesh belt, (d) a step of dehydrating the raw material mixture laminated on the mesh belt, and (e) a drying step.

First, when describing (a) the step of preparing raw materials in more detail, this step is a step of individually preparing a coniferous pulp, a PET fiber, a binder fiber, and a solvent.

Here, the solvent, which allows the respective raw materials to be uniformly mixed with each other, may be an aqueous solution having a wet strengthening agent dissolved therein (hereinafter referred to as an aqueous wet strengthening agent solution). As an example, water and the wet strengthening agent may be mixed in a weight ratio of 9,000 to 11,000:1 to 5.

Meanwhile, concrete physical properties and functions related to the coniferous pulp, the PET fiber, the binder fiber, and the wet strengthening agent were previously described, and therefore a duplicative description thereof will be omitted.

(b) The step of mixing the prepared raw materials to prepare a raw material mixture is a step of putting the coniferous pulp, the PET fiber, and the binder fiber in the aqueous wet strengthening agent solution and stirring the same to prepare a slurry type raw material mixture.

At this time, it is preferable to mix 9,500 to 10,500 parts by weight of the aqueous wet strengthening agent solution, 60 to 75 parts by weight of the coniferous pulp, 10 to 20 parts by weight of the PET fiber, and 10 to 20 parts by weight of the binder fiber with each other.

Meanwhile, it is preferable for the aqueous wet strengthening agent solution to be heated to 25 to 45° C. in advance. If the temperature of the aqueous wet strengthening agent solution is lower than the above range, dispersibility and dehydration efficiency are low, and dispersibility of the wet strengthening agent is low. If the temperature of the aqueous wet strengthening agent solution is higher than the above range, on the other hand, the raw material mixture and a mesh in step (c) are burdened. For these reasons, it is preferable for the temperature of the solvent to be within the above range.

The raw material mixture prepared in the above mixing ratio is stirred at a speed of 900 to 1100 RPM for about 15 to 25 minutes, whereby a raw material mixture slurry is obtained.

(c) The step of laminating the raw material mixture on a mesh belt is a step of laminating the slurry type raw material mixture prepared in the above mixing ratio on a mesh belt. Specifically, the raw material mixture is supplied to a mesh belt that moves at a speed of 10 to 20 m/min, and the amount of supply is preferably 2,500 L/min.

(d) The step of dehydrating the raw material mixture laminated on the mesh belt is a step of dehydrating the raw material mixture laminated on the mesh belt to primarily remove water from the aqueous wet strengthening agent solution.

At this time, dehydration is performed through a dehydration process of performing primary vacuum dehydration the moment the raw material mixture is laminated on the mesh belt to dehydrate the raw material mixture and additionally performing secondary vacuum dehydration.

In the primary vacuum dehydration process, vacuum pressure is applied through four steps. A vacuum pressure of 0 to 5 cmHg is applied in a first step, a vacuum pressure of 10 to 20 cmHg is applied in a second step, a vacuum pressure of 30 to 40 cmHg is applied in a third step, and a vacuum pressure of 50 to 65 cmHg is applied in a fourth step. Through the above dehydration process, binding between fibers is induced, and, as a result, non-woven fabric having porosity is formed.

In the secondary vacuum dehydration process, a vacuum pressure of about 18 to 22 cmHg is applied to remove residual moisture and at the same time to achieve denser binding between the fibers.

Finally, (e) the drying step, which is a step of completely removing residual moisture, is achieved by allowing the raw material mixture to sequentially pass through a hot-air dryer and a drum dryer. Specifically, primary drying in a hot-air dryer operated at 100 to 170° C., more preferably 110 to 130° C., secondary drying using hot air of 135 to 145° C., tertiary drying using hot air of 150 to 190° C., and quaternary drying in a drum dryer of 135 to 145° C. are sequentially performed.

If drying is performed at a high temperature in the initial stage of the drying step, drying is rapidly performed, whereby contraction or paper fracture occurs. If drying is performed at a low temperature in the initial stage of the drying step, on the other hand, complete binding of the binder fiber is not performed and the amount of residual moisture after winding is large, whereby negative influences, such as the occurrence of fluff or weakening of binding force, are exerted in a subsequent process. Consequently, it is preferable to perform drying under the four-step drying conditions from the primary drying to the quaternary drying.

Subsequently, a process of slitting the raw material mixture using a slitting machine and storing the slit raw material mixture may be further performed as needed.

Hereinafter, the present invention will be described in more detail with reference to examples and an experimental example. However, the following examples and experimental example merely illustrate the present invention, and the content of the present invention is not limited to the following examples and experimental example.

EXAMPLES

Example 1

5 kg of an epoxidized polyamide resin, as a wet strengthening agent, was added to 10,000 L of water heated to 30° C. to prepare an aqueous wet strengthening agent solution. Subsequently, 15 kg of a PET fiber having an average diameter of 2 de and a length of 3 mm, 70 kg of a coniferous pulp having an average length of 2.3 mm, and 15 kg of a low melting polyethylene terephthalate having an average diameter of 2 de and a length of 5 to 7 mm (a melting point of 120° C., two kinds of polyethylene terephthalate are disposed in a sheath-core structure) were mixed in the prepared aqueous wet strengthening agent solution and were stirred for about 20 minutes to prepare a raw material mixture.

The prepared raw material mixture was laminated on a microfiber mesh belt. At this time, the feed rate of the mesh belt was 15 m/min, and the raw material mixture was uniformly supplied at 2,500 L/min.

In addition, the moment the raw material mixture was laminated on the mesh belt, first-step natural dehydration was performed at a vacuum pressure of 0 cmHg, and then primary dehydration was performed at a second-step vacuum pressure of 10 cmHg, a third-step vacuum pressure of 30 cmHg, and a fourth-step vacuum pressure of 50 cmHg.

After the primary dehydration, secondary dehydration was performed at a vacuum pressure of 20 cmHg.

Finally, primary drying in a hot-air dryer operated at 110 to 130° C., secondary drying at 135 to 145° C., tertiary drying at 150 to 190° C., and quaternary drying in a drum dryer of 135 to 145° C. were performed to remove residual moisture, whereby a sample pad for diagnosis kits was manufactured.

Example 2

A sample pad for diagnosis kits was manufactured under the same conditions as in Example 1 except that 60 kg of a coniferous pulp, 20 kg of a PET fiber, 20 kg of a binder fiber, and 3 kg of a wet strengthening agent were used in a raw material mixture.

Example 3

A sample pad for diagnosis kits was manufactured under the same conditions as in Example 1 except that 75 kg of a coniferous pulp, 10 kg of a PET fiber, and 3 kg of a wet strengthening agent were used in a raw material mixture.

Example 4

A sample pad for diagnosis kits was manufactured under the same conditions as in Example 1 except that 65 kg of a coniferous pulp, 20 kg of a binder fiber, and 1 kg of a wet strengthening agent were used in a raw material mixture.

COMPARATIVE EXAMPLES

Comparative Example 1

A sample pad for diagnosis kits was manufactured under the same conditions as in Example 1 except that 60 kg of a coniferous pulp, 35 kg of a PET fiber, and 5 kg of a binder fiber were used in a raw material mixture.

Comparative Example 2

A sample pad for diagnosis kits was manufactured under the same conditions as in Example 1 except that 30 kg of a coniferous pulp, 20 kg of a PET fiber, 20 kg of a glass fiber having an average diameter of 9 to 11 μm and a length of 3.0 to 6.0 mm, and 30 kg of a binder fiber were used in a raw material mixture without addition of a wet strengthening agent.

Comparative Example 3

A sample pad for diagnosis kits was manufactured under the same conditions as in Example 1 except that 70 kg of a coniferous pulp, 5 kg of a glass fiber having an average diameter of 9 to 11 μm and a length of 3.0 to 6.0 mm, and 25 kg of a binder fiber were used in a raw material mixture without addition of a PET fiber and a wet strengthening agent.

Comparative Example 4

A sample pad for diagnosis kits was manufactured under the same conditions as in Example 1 except that 50 kg of a coniferous pulp, 40 kg of a PET fiber, 10 kg of a binder fiber, and 3 kg of a wet strengthening agent were used in a raw material mixture.

Comparative Example 5

A sample pad for diagnosis kits manufactured by company A and currently for sale was used.

TABLE 1

| | Water | Coniferous pulp | PET fiber | Glass fiber | Binder fiber | Wet strengthening agent |
|---|---|---|---|---|---|---|
| Example 1 | 10,000 L | 70 kg | 15 kg | — | 15 kg | 5 kg |
| Example 2 | 10,000 L | 60 kg | 20 kg | — | 20 kg | 3 kg |
| Example 3 | 10,000 L | 75 kg | 10 kg | — | 15 kg | 3 kg |
| Example 4 | 10,000 L | 65 kg | 15 kg | — | 20 kg | 1 kg |
| Comparative Example 1 | 10,000 L | 60 kg | 35 kg | — | 5 kg | 5 kg |

TABLE 1-continued

| | Water | Coniferous pulp | PET fiber | Glass fiber | Binder fiber | Wet strengthening agent |
|---|---|---|---|---|---|---|
| Comparative Example 2 | 10,000 L | 30 kg | 20 kg | 20 kg | 30 kg | — |
| Comparative Example 3 | 10,000 L | 70 kg | — | 5 kg | 25 kg | — |
| Comparative Example 4 | 10,000 L | 50 kg | 40 kg | — | 10 kg | 3 kg |
| Comparative Example 5 | — | — | — | — | — | — |

* Comparative Example 5 is a company A product for sale.

Experimental Example

Physical properties of the sample pads manufactured according to Examples 1 to 4 and Comparative Examples 1 to 5 were measured, and the results thereof are shown in Table 2.

For the wicking rate, a sample having a width of 2.5 cm and a length of 17 cm was vertically soaked in a sample solution by about 1 cm and time taken until the sample solution was absorbed by the sample to a point of 4 cm was measured according to AATCC Test Method 197-2012 (Vertical Wicking Test) Standards.

In the wicking test, the weight of a circular sample having a diameter of 2 inches was measured after being completely dried and the weight of the sample was measured after being soaked in the sample solution according to ASTM D57 Standards. Smoothness of the sample was observed with the naked eye.

TABLE 2

| | Wicking rate (s/4 cm) | Water absorption ($mg/cm^2$) | Smoothness |
|---|---|---|---|
| Example 1 | 25 | 66 | Good |
| Example 2 | 24 | 63 | Good |
| Example 3 | 26 | 65 | Good |
| Example 4 | 28 | 62 | Good |
| Comparative Example 1 | 19 | 58 | Bad |
| Comparative Example 2 | 42 | 48 | Bad |
| Comparative Example 3 | 24 | 53 | Good |
| Comparative Example 4 | 15 | 51 | Bad |
| Comparative Example 5 | 86 | 38 | Good |

As summarized in Table 2, it can be seen that, for the sample pads manufactured using the manufacturing methods according to Examples 1 to 4 of the present invention, the wicking rates were 24 to 28 s/4 cm and water absorptions were 62 to 66 $g/cm^2$, i.e. two parameters were excellent.

In contrast, for the sample pad manufactured using the manufacturing method according to Comparative Example 1, the wicking rate was too fast and the water absorption was low, since the content of the PET fiber was excessive while the content of the binder fiber was deficient.

For the sample pad according to Comparative Example 2, the content of relatively long fibers was high during the manufacturing process, since the content of the coniferous pulp was deficient while the content of the glass fiber and the content of the binder fiber were excessive, whereby the surface smoothness was not good, the wicking rate was too slow, and the water absorption was low.

For the sample pad according to Comparative Example 3, water absorption necessary to be used for diagnosis kits was not obtained, since the content of the PET fiber and the content of the wet strengthening agent were deficient while the content of the binder fiber was too high.

For the sample pad according to Comparative Example 4, the wicking rate and the water absorption deviate from appropriate ranges thereof, since the content of the PET fiber was excessive, and this sample pad was not appropriate as a sample pad for diagnosis kits, since the surface smoothness was bad.

Meanwhile, for the sample pad according to Comparative Example 5, which was a company A product for sale, the wicking rate was too slow, and the water absorption was very low.

The present invention has been described above based on the preferred embodiments thereof. A person having ordinary skill in the art to which the present invention pertains will understand that the present invention can be implemented in modified forms without departing from intrinsic characteristics of the present invention. Therefore, the disclosed embodiments must be considered from an illustrative point of view, rather than a limited point of view. It should be interpreted that the scope of the present invention be defined by the appended claims, not by the above description, and the scope equivalent thereto be included in the present invention.

The invention claimed is:

1. A method of manufacturing a sample pad, the method comprising:
   (a) preparing 60 to 75 parts by weight of a coniferous pulp, 10 to 20 parts by weight of a polyethylene terephthalate (PET) fiber, 15 to 20 parts by weight of a binder fiber, and 1 to 5 parts by weight of a wet strengthening agent as raw materials;
   (b) mixing the raw materials to prepare a raw material mixture;
   (c) laminating the raw material mixture on a mesh belt;
   (d) dehydrating the raw material mixture laminated on the mesh belt; and
   (e) a drying operation performed after (d),
   wherein (b) comprises:
      60 to 75 parts by weight of the coniferous pulp, 10 to 20 parts by weight of the PET fiber, and 15 to 20 parts by weight of the binder fiber are mixed in 9,000 to 11,000 parts by weight of an aqueous wet strengthening agent solution, and
      the aqueous wet strengthening agent solution comprises 9,000 to 11,000 parts by weight of water and 1 to 5 parts by weight of an epoxy resin,
   wherein (d) comprises:
      a primary vacuum dehydration operation of sequentially applying vacuum pressures of about 0 to 5 cmHg in a first operation, about 10 to 20 cmHg in a second operation, about 30 to 40 cmHg in a third operation, and about 50 to 65 cmHg in a fourth operation; and
      a secondary vacuum dehydration operation of applying a vacuum pressure of about 18 to 22 cmHg, and
   wherein (e) comprises:
      hot air drying at about 110 to 130° C., hot air drying at about 135 to 145° C., hot air drying at about 100 to 110° C., and hot air drying at about 135 to 145° C. are sequentially performed.

2. The method according to claim 1, wherein
in (b), 60 to 75 parts by weight of the coniferous pulp, 10 to 20 parts by weight of the PET fiber, and 15 to 20 parts by weight of the binder fiber are mixed in 9,500 to 10,500 parts by weight of the aqueous wet strengthening agent solution.

3. The method according to claim 1, wherein in (e), the drying operation alternatively performed is a primary hot air drying at about 110 to 130° C., a secondary hot air drying at about 135 to 145° C., a tertiary hot air drying at about 150 to 190° C., and quaternary hot air drying at about 135 to 145° C. being sequentially performed.

4. The method according to claim 1, wherein the vacuum pressures of the first operation is 0 cmHg, the second operation is 10 cmHg, the third operation is 30 cmHg, and the fourth operation is 50 cmHg.

5. The method according to claim 1, wherein the vacuum pressure of the secondary vacuum dehydration operation is 20 cmHg.

* * * * *